United States Patent [19]

Pinori et al.

[11] Patent Number: 4,560,505

[45] Date of Patent: Dec. 24, 1985

[54] RETRO-INVERSO ANALOG OF THE (5-14) DECAPEPTIDE OF EQUINE ANGIOTENSINOGEN, AS A SPECIFIC RENIN INHIBITOR WITH HIGH RESISTANCE TO ENZYMATIC HYDROLYSIS

[75] Inventors: Massimo Pinori; Antonio S. Verdini, both of Monterotondo, Italy

[73] Assignee: ENI - Ente Nazionale Idrocarburi, Rome, Italy

[21] Appl. No.: 612,798

[22] Filed: May 22, 1984

[30] Foreign Application Priority Data

May 25, 1983 [IT] Italy ................................ 21281 A/83

[51] Int. Cl.⁴ ............................................ C07C 103/52
[52] U.S. Cl. ................................................ 260/112.5 R
[58] Field of Search ................................... 260/112.5 R

[56] References Cited

U.S. PATENT DOCUMENTS 4,424,207 1/1984 Szelke et al. ................. 260/112.5 R
4,439,360 3/1984 Verdini et al. ............... 260/112.5 R

FOREIGN PATENT DOCUMENTS 0097994 1/1984 European Pat. Off. .

OTHER PUBLICATIONS

Pallai et al., *American Peptide Symposium*, (7th: 1981: U. of Wisconsin), "Configuration of Substituted Malonyl and Gem-Diamino Derivatives of Peptides", pp. 85-88.
Burton et al., *Medical Sciences*, vol. 77, No. 9, 5476-5479, (1980).
Cody et al., *Biochemical and Biophysical Research Communications*, vol. 97, No. 1, 230-235, (1980).
Radhakrishna et al., *J. Org. Chem.*, vol. 44, No. 10, 1746-1747, (1979).

*Primary Examiner*—Delbert R. Phillips
*Assistant Examiner*—F. T. Moezie
*Attorney, Agent, or Firm*—Hedman, Gibson, Costigan & Hoare

[57] ABSTRACT

There is provided an analog of the (5-14) decapeptide of equine angiotensinogen which is partially inverted at the Phe-Val bond, and which has the formula Pro—His—Pro—Phe—His—Phe—NH—

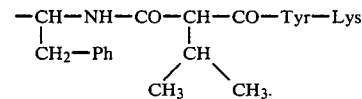

This retro-inverso analog inhibits renin with high resistance to enzymatic degradation and it can be used in the treatment of renin-dependent hypertension.

3 Claims, No Drawings

RETRO-INVERSO ANALOG OF THE (5-14) DECAPEPTIDE OF EQUINE ANGIOTENSINOGEN, AS A SPECIFIC RENIN INHIBITOR WITH HIGH RESISTANCE TO ENZYMATIC HYDROLYSIS

FIELD OF THE INVENTION

This invention relates to an analogue of the (5-14) decapeptide of equine angiotensinogen which is partly retro-inverted at the Phe—Val bond, is a specific renin inhibitor with high resistance to enzymatic hydrolysis, and has prolonged in vivo activity.

BACKGROUND OF THE INVENTION

Renin is one of the enzymatic components of the renin-angiotensin system illustrated hereinafter, the products of which perform physiologically important roles in maintaining cardiovascular homeostasis and contribute to the increase in arterial pressure in various hypertensive states [S. Oparil and E. Haber, New England J. Med. 291, 389 (1974); W. S. Peart, New England J. Med. 292, 302 (1975); E. Haber et al., Clin. Sci. Mol. Med. 48, 49 s (1975); J. O. Davis, Clin. Sci. Mol. Med. 48, 30 (1975)].

Asp-Arg-Val-Tyr-Ile-His-Pro-Phe-His-Leu-Leu-Val-Tyr-Ser (Angiotensinogen)

↓ Renin

Asp-Arg-Val-Tyr-Ile-His-Pro-Phe-His-Leu (Angiotensin I)

↓ Converting enzyme (ACE)

Asp-Arg-Val-Tyr-Ile-His-Pro-Phe + His-Leu (Angiotensin II)

↓ endopeptidases

← carboxypeptidase fragments  α-aminopeptidases

Arg-Val-Tyr-Ile-His-Pro-Phe (Angiotensin III)

Renin, produced and released by the kidney juxtaglomerular cells, reacts with the renin substrate (angiotensinogen) to produce angiotensin I, an inactive decapeptide, which itself is converted, mainly in the lung, to angiotensin II by the angiotensin converting enzyme (ACE).

Angiotensin II is the most powerful endogenous substance of pressor action which has been known up to the present time, and participates in regulating the release of renin by means of a direct feedback mechanism.

The renin-angiotensin system also constitutes one of the main mechanisms for controlling the secretion of aldosterone from the suprarenal cortex, and the release of aldosterone is known to determine retention of $Na^+$, fluids and caliuresis.

Compounds which are inhibitors of the renin-angiotensin system are currently used for treating hypertension.

Said compounds have the drawback of producing side effects such as the onset of compensatory hyper-reninemia.

Moreover, recent experimental studies have shown that renin is present and is synthesized in the vascular smooth musculature, and could therefore play a not insignificant role im maintaining blood pressure. It has therefore been considered opportune to research the field of specific renin inhibitors for treating hypertension.

Said inhibitors pertain to the following three classes:
(1) pepstatin and analogues
(2) lipids and phospholipids
(3) renin substrate analogues However, pepstatin and analogues are very effective in reducing blood pressure only in animal hypertension models ($I_{50}$ 0.1 μM), are ineffective in normotensive rats, and also have poor inhibition specificity, in that they act not only on renin but also on other acid proteases such as pepsin, isorenins and cathepsin D. The anti-hypertensive activity of lipids and phospholipids, which has been repeatedly observed in vitro, has recently been questioned, as has their importance as physiological regulators of the renin-angiotensin system. [M. J. Antonaccio and D. W. Cushman, Federation Proc., 40, 2275 (1981)].

Much interest has however been aroused by the compounds of the third class, the synthetic peptide inhibitors, in the form of structural analogues of renin substrate fragments incorporating the bonds $Leu^{10}$—$Leu^{11}$ and $Leu^{10}$—$Val^{11}$ hydrolysed by renin. Said compounds are very potent inhibitors ($I_{50}$ from 5.9 μM to 10 μM) and are highly specific. [J. Burton et al., Proc. Acad. Sci. U.S.A., 77, 5476 (1980); M. Szelke et al., European Patent Application No. 0-045-665, (1982); M. Szelke et al., Nature, 299, 555 (1982)]. Of these, the octapeptide His—Pro—Phe—His—Leu—Val—Ile—His and the decapeptide Pro—His—Pro—Phe—His—Leu—Val—Ile—His—Lys of the N-terminal sequence of human angiotensinogen, in which the hydrolysable Leu—Val bond has been reduced to —$CH_2$—NH— in order to block hydrolysis by the renin, and the decapeptide Pro—His—Pro—Phe—His—Phe—Phe—Val—Tyr—Lys of the N-terminal sequence of equine angiotensinogen has been synthesised.

However, this latter decapeptide, which is a specific inhibitor of human renin in vitro and an effective in vivo antihypertensive, has a very short action duration (about 4 minutes) and this represents a limitation to its clinical application (J. Burton, U.S. Pat. No. 4,269,827).

DESCRIPTION OF THE INVENTION

An inhibitor peptide which is specific for renin and has a high resistance to enzymatic hydrolysis and a prolonged time of action has now been discovered, and forms the subject matter of the present invention.

The use of renin inhibitors with prolonged action has the following consequences:

(1) it prevents the onset of compensatory hyper-reninemia, which generally occurs during the use of current inhibitors of the renin-angiotensin system;

(2) it enables long-duration in vivo experiments to be carried out in studies on chronic renin-dependent hypertensive forms. One of the main causes of the limited in vivo stability of the decapeptide and thus of its nonpersistent antihypertensive action seems to be connected with the ease with which it is hydrolysed by the action of the renin itself and of the other peptidases of the blood plasma.

Consequently, in order to obtain adequate protection of the peptide substances against the proteolytic action of proteases, it has been found very advantageous to use the method of retro-inverting those peptide bonds which are most susceptible to enzymatic hydrolysis.

Inverting the direction of the peptide bonds

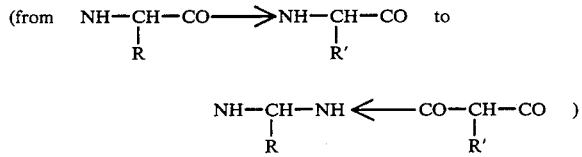

as described in the U.S. Applns. Ser. Nos. 448,831, 448,832, EP Appln. Publ. No. 0097994, It. Appln. Nos. 20926A/82, 23417A/82 produces analogues known generically as "retro-inverso peptides" which are structural isomers of the reference peptides and as such preserve their biological activity while being generally more resistant to enzymatic hydrolysis.

According to the present invention, we have inverted the Phe—Val bond of the decapeptide Pro—His—Pro—Phe—His—Phe—Phe—Val—Tyr—Lys, which is adjacent to the hydrolytic action site of renin, to obtain an analogue capable of inhibiting the enzyme with an in vivo activity more prolonged than that of the inhibitor with all its peptide bonds normal.

The inversion of a single peptide bond in the sequence involves transforming the two engaged amino acid residues in order to form the inverted bond, and in particular transforming the amino acid residue closest to the amino end of the reference peptide into a gem-diamino residue, and transforming the amino acid residue closest to the carboxyl end into a malonyl or 2-substituted malonyl residue. [Goodman M. et al., Acc. Chem. Res. 12 (1979)].

Incorporating the malonyl or 2-substituted malonyl residues into the peptide skeleton does not present special problems, whereas incorporating gem-diamino residues generally requires delicate synthesis manipulations, which have been accomplished as described in the aforesaid preceding cited patent applications by the use of 1,1-bis(trifluoroacetoxy)iodobenzene (TIB). This reagent had been previously used for the direct conversion of primary simple structure amides into amines without the need for isolating or capturing the intermediate isocyanate [Radhakrishna A. S. et al., J. Org. Chem. 44, 1746 (1979)].

The retro-inverso peptide of the present patent application is represented by the formula:

where the amino acids are all of L configuration, the asymmetric carbon of the gem-diamino residue has the same configuration as the L-phenylalanine, and the asymmetric carbon of the malonyl residue can possess R or S configuration, or a mixture of the two configurations.

The peptide can be prepared conveniently by synthesis entirely in the solid phase. The residues 7 and 8 can be firstly be inserted in the form of 2-isopropyl-malonyl-D-phenylalaninamide, and the the primary amide can be converted into amine by the action of 1,1-bis(trifluoroacetoxy)iodobenzene. The synthesis can be continued in the usual manner for synthesising peptides in the solid phase. This consists, as known to experts of the art, in constructing the sequence by adding the individual amino acids in successive stages on insoluble polymer matrices which are swellable in the reaction medium, and to which the peptide remains bound until termination of the synthesis, and from which it is released by treatment with a suitable reagent.

The polymer used in the synthesis according to the present patent is constituted by beads of polyamide resin which has been suitably functionalized with substituted benzyl alcohol residues [R. Arshady et al., J. Chem. Soc., Perkin I 529 (1981)].

The first lysine amino acid residue, activated separately under suitable conditions, is bound to these residues by an ester linkage, as a symmetrical anhydride. The substituted benzyl alcohol residue connecting the peptide to the resin insoluble during the synthesis was chosen in such a manner that the peptide could be detached from the resin on termination of the synthesis by treatment with trifluoroacetic acid.

The tests to determine the renin inhibition by the peptide analogue according to the present invention can be conducted as described by Millar and collaborators [J. A. Millar et al., Clinica Chim. Acta 101, 5 (1980)]. In this test, the rate of generation of angiotensin I from human angiotensinogen by human plasmatic renin at pH 7.0 is measured by radioimmunoassay of antibody binding. The rate of generation of angiotensin I in the presence of the inhibitor can be expressed generally as a percentage of that measured in the absence of inhibitor.

The increased stability of the retro-inverso peptide to peptidases compared with the peptide without inverted bonds under the inhibition test conditions can be evaluated either in the absence or in the presence of peptidase inhibitors such as EDTA, o-phenanthroline, benzamidine hydrochloride and trasylol, and either with or without preincubation in the human plasma. The retro-inverso peptide of the present invention is a potent selective renin inhibitor with a duration of action which is more prolonged than that of the peptide with all its peptide bonds normal.

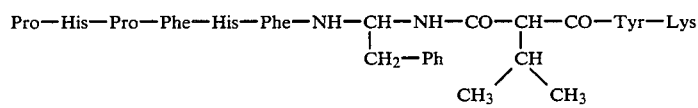

EXAMPLE

Preparation of the peptide

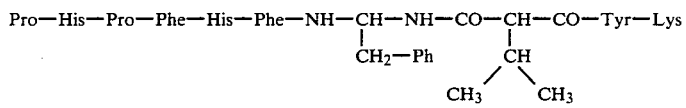

The synthesis was conducted in the solid phase by the method described by Sheppard and collaborators [E. Atherton et al., J. Chem. Soc. Perkin I, 538 (1981)], with certain modifications.

1 g of polymer support constituted by beads of polydimethylamide-co-acryloylsarcosine methyl ester cross-linked with N,N'-ethylenebis-acrylamide, was activated by treatment with 1,2-diaminoethane. The activated resin was reacted with 1.8 mmoles of (Fmoc Nle)$_2$O and then, after removing the Fmoc by treatment with 20% piperidine in dimethylformamide (DMF), it was acylated with 1.8 mmoles of 2,4,5-trichlorophenol-p-hydroxymethylbenzoate.

The resin modified in this manner contained 0.525 mmoles/g of norleucine.

The ester linkage with the first amino acid was formed by treating the modified resin for 30 minutes with 1.8 mmoles of (Fmoc Lys)$_2$O dissolved in 16 ml of DMF in the presence of 1.8 mmoles of N-methylmorpholine and 0.18 mmoles of 4-dimethylaminopyridine. This reaction, and the subsequent ones until the synthesis of the entire hexapeptide was complete, was conducted in the reaction vessel of an automatic Beckman ® synthesizer, model 990B. The subsequent amino acids were introduced sequentially into the polymer in the order described in Table 1, following one of the procedures of Table 2.

The symmetrical anhydrides of the protected amino acids were preformed at the moment of acylation: 3.6 mmoles of protected amino acid were reacted with 1.8 mmoles of N,N'-dicyclohexylcarbodiimide in CH$_2$Cl$_2$ at ambient temperature for 10 minutes, the dicyclohexylurea which formed was filtered off, the CH$_2$Cl$_2$ was evaporated under vacuum, and the symmetrical anhydride was redissolved in 16 ml of DMF.

For each acylation, completion of the formation of the amide bond was verified by reacting a sample of resin with ninhydrin by the method of Kaiser [E. Kaiser, Anal. Biochem. 34, 595 (1970)]. Amino acid analysis was conducted on samples hydrolysed for 18 hours at 110° C. with HCl to constant boiling point, in the presence of phenol, in closed vials under vacuum.

The complete conversion of the D-phenylalaninamide into the corresponding gem-diamino residue was verified by the disappearance of the phenylalanine in the amino acid analysis conducted on a sample of resin withdrawn after the treatment with TIB. After adding the final amino acid, the resin was washed with ethyl ether, dried and then suspended in 95% trifluoroacetic acid for 3 hours. After filtering the resin off and washing it with 2N acetic acid, the solution containing the peptide was lyophilised. The peptide was then dissolved in 25 ml of AcOH (80%), and 500 mg of 10% palladium metal on activated carbon and 500 mg of ammonium formate were added to the solution. [M. K. Anwer and A. F. Spatola, Synthesis, 929 (1980)].

After 2 hours, the Pauly reaction indicated complete removal of the histadine protector group. The mixture was then centrifuged and the solution was lyophilised several times after diluting with water. The crude peptide was chromatographed at pH 7.0 on a column of carboxymethylcellulose (CM-52) eluting with a linear gradient of ammonium acetate in the concentration range of 0.05N to 0.5N. The fractions containing the peptide were lyophilised and again chromatographed at pH 4.5 on a column of Sephadex SP C25, eluting with a linear gradient of ammonium acetate in the concentration range of 0.25N to 1N. The fractions containing the peptide were pooled and lyophilised.

Amino acid analysis: Pro, 2.07 (2); His, 2.10 (2); Phe, 2.10 (2); Tyr, 0.99 (1); Lys, 1.00 (1).

The peptide obtained, consisting of a mixture of two diastereoisomers as the result of introducing the 2-isopropylmalonyl residue in raceme form into the chain, showed two peaks on high pressure chromatographic analysis on an analytical Hibar RP-18 column (5 μM), the eluent being acetonitrile/H$_2$O (38/62) containing trifluoroacetic acid (0.1%). The peptide sample showed a single spot (ninhydrin test and test with Pauly reagent) under high voltage electrophoresis on a thin layer of microcrystalline cellulose (buffers used: formic acid-acetic acid, pH 2.1; sodium acetate-acetic acid, pH 3.5).

Separation of diastereoisomers

The mixture of the two diastereoisomers was resolved by reverse-phase semipreparative high pressure liquid chromatography experiments, using a column filled with Lichroprep ® RP-18 (Merck, Darmstadt) of dimensions 7.8×30 mm and eluting for the first 20 minutes with an acetonitrile/H$_2$O (26/74) mixture containing trifluoroacetic acid (0.1%), followed for a further 8 minutes with an acetonitrile/H$_2$O (39/61) mixture containing trifluoroacetic acid (0.1%). Separation of the individual diastereoisomers was conducted on various sample portions each containing about 0.5 micromoles of peptide. The fractions corresponding to the two isomers were lyophilised and again checked by high pressure liquid chromatography experiments on an analytical column.

Amino acid analysis: Isomer A: Pro, 1.83 (2); His, 1.99 (2); Phe, 1.99 (2); Tyr, 0.94 (1); Lys, 1.00 (1); Isomer B: Pro, 1.86 (2); His, 1.99 (2); Phe, 2.05 (2); Tyr, 0.96 (1); Lys, 1.00 (1).

TABLE 1

| ORDER OF ADDING THE AMINO ACIDS USED IN THE SYNTHESIS, AND THE PROCEDURE USED ||
|---|---|
| Amino acid derivative | Procedure |
| (1) FMOC—Lys(Boc)—OH | — |
| (2) FMOC—Tyr(OBu$^t$)—OH | A |
| CH$_3$ COOH | |
| (3) CH—CH | B |
| CH$_3$ CO—D-Phe—NH$_2$ | |
| (4) FMOC—PheOH | C |
| (5) FMOC—His (N—Bom)—OH* | A |
| (6) FMOC—Phe—OH | A |
| (7) FMOC—Pro—OH | A |
| (8) FMOC—His (N—Bom)—OH | A |
| (9) Boc—Pro—OH | A |

Bom = N—benzyloxymethyl (T. Brown, J. N. Jones, J. D. Richards, J. Chem. Soc., Perkin Trans I, 1553 (1982))

TABLE 2

PROCEDURES USED IN THE COURSE OF THE SOLID PHASE SYNTHESIS

| | | |
|---|---|---|
| (1) 5 washes with DMF | (1) 5 washes with DMF | (1) 5 washes with DMF |
| (2) 2 treatments with 20% piperidine in DMF | (2) 2 treatments with 20% piperidine in DMF | (2) 10 washes with DMF/H$_2$O (1:1) |
| (3) 10 washes with DMF | (3) 10 washes with DMF | (3) treatment with 1,1-bis(trifluoroacetoxy)-iodobenzene (TIB) for 1 hour |
| (4) acylation via symmetrical anhydride | (4) acylation with dicyclohexylcarbodiimide and N—hydroxybenzotriazole | (4) 5 washes with DMF/H$_2$O (1:1) |
| (5) 5 washes with DMF | (5) 5 washes with DMF | (5) treatment with TIB for 16 hours |
| | | (6) 15 washes with DMF |
| | | (7) 3 treatments with 10% diisopropylethylamine in DMF |
| | | (8) 5 washes with DMF |
| | | (9) acylation via symmetrical anhydride |
| | | (10) 5 washes with DMF |

We claim:

1. A peptide partially retro-inverted at the Phe—Val bond, as a specific renin inhibitor and possessing high resistance to enzymatic hydrolysis and prolonged in vivo inhibition activity, of the following formula:

Pro—His—Pro—Phe—His—Phe—NH—

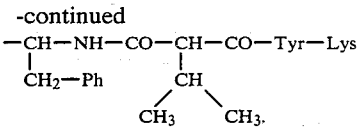

2. A peptide as claimed in claim 1, wherein the gem-diamino residue possesses S configuration and the malonyl residue possesses S configuration.

3. A peptide as claimed in claim 1, wherein the gem-diamino residue possesses S configuration and the malonyl residue possesses R configuration.

* * * * *